US011357567B2

(12) United States Patent
Cohen et al.

(10) Patent No.: US 11,357,567 B2
(45) Date of Patent: **\*Jun. 14, 2022**

(54) ONCOLOGICAL AMELIORATION BY IRRADIATION AND/OR ENSONIFICATION OF TUMOR VASCULARIZATION

(71) Applicants: Nathan Cohen, Belmont, MA (US); Alexander J. Shelman-Cohen, Cambridge, MA (US)

(72) Inventors: Nathan Cohen, Belmont, MA (US); Alexander J. Shelman-Cohen, Cambridge, MA (US)

(\*) Notice: Subject to any disclaimer, the term of this patent is extended or adjusted under 35 U.S.C. 154(b) by 0 days.

This patent is subject to a terminal disclaimer.

(21) Appl. No.: 16/866,956

(22) Filed: May 5, 2020

(65) Prior Publication Data

US 2020/0261148 A1 Aug. 20, 2020

Related U.S. Application Data

(63) Continuation of application No. 12/825,297, filed on Jun. 28, 2010, now Pat. No. 10,639,096.

(Continued)

(51) Int. Cl.
*A61B 18/14* (2006.01)
*A61N 7/02* (2006.01)
(Continued)

(52) U.S. Cl.
CPC ............ *A61B 18/1477* (2013.01); *A61N 7/02* (2013.01); *A61B 18/18* (2013.01); *A61B 2018/00083* (2013.01); *A61B 2018/00196* (2013.01); *A61B 2018/00577* (2013.01); *A61B 2018/1425* (2013.01); *A61B 2218/002* (2013.01)

(58) Field of Classification Search
CPC ............ A61B 18/18; A61B 2018/1807; A61B 18/1815; A61B 2018/1823; A61B 2018/183; A61B 2018/1838; A61B 2018/1846; A61B 2018/1853;
(Continued)

(56) References Cited

U.S. PATENT DOCUMENTS 4,471,787 A 9/1984 Bentall
5,019,076 A 5/1991 Yamanashi et al.
(Continued)

*Primary Examiner* — Jaymi E Della
(74) *Attorney, Agent, or Firm* — Daly, Crowley, Mofford & Durkee, LLP

(57) ABSTRACT

Techniques are disclosed, including methods and systems/apparatus, that can be used to treat cancerous tissue by exploiting the fact that such tissues have vascular branching with fractal descriptions and fractal dimensions, which are different from those found in normal soft tissue vascular branching. Such fractal branching of diseased tissue can produce resonances, or preferential energy absorption, when irradiated by either ultrasound and/or radio frequencies of EM energy; these resonances are not shared by the vascularization in normal soft tissue. Accordingly, one or more specific arrangements of multiband radiation (e.g., RF and/or ultrasonic) used to irradiate such diseased tissue will cause heating and possibly localized necropsy of tumor blood vessels, with little or minimal damage to surrounding healthy tissue. Embodiments can utilize ablation devices in conjunction with RF and/or ultrasonic sources. Embodiments can further utilize chemotherapy (before, during, or after hyperthermic treatment) for enhancing cancer treatment.

2 Claims, 9 Drawing Sheets

Related U.S. Application Data

(60) Provisional application No. 61/269,622, filed on Jun. 27, 2009.

(51) Int. Cl.
*A61B 18/00* (2006.01)
*A61B 18/18* (2006.01)

(58) Field of Classification Search
CPC .... A61B 2018/1861; A61B 2018/1869; A61B 2018/1876; A61B 2018/1884; A61N 5/00
See application file for complete search history.

(56) References Cited

U.S. PATENT DOCUMENTS

| | | |
|---|---|---|
| 5,385,544 A | 1/1995 | Edwards et al. |
| 5,472,441 A | 12/1995 | Edwards et al. |
| 5,599,345 A | 2/1997 | Edwards et al. |
| 6,104,349 A | 8/2000 | Cohen |
| 6,127,977 A | 10/2000 | Cohen |
| 6,140,975 A | 10/2000 | Cohen |
| 6,445,352 B1 | 9/2002 | Cohen |
| 6,452,553 B1 | 9/2002 | Cohen |
| 6,476,766 B1 | 11/2002 | Cohen |
| 6,985,122 B2 | 1/2006 | Cohen |
| 7,019,695 B2 | 3/2006 | Cohen |
| 7,126,537 B2 | 10/2006 | Cohen |
| 7,145,513 B1 | 12/2006 | Cohen |
| 7,179,254 B2 | 2/2007 | Pendekanti et al. |
| 7,190,318 B2 | 3/2007 | Cohen |
| 7,215,290 B2 | 5/2007 | Cohen |
| 7,256,751 B2 | 8/2007 | Cohen |
| 7,326,201 B2 | 2/2008 | Fjield et al. |
| 7,345,642 B2 | 3/2008 | Cohen |
| 7,456,799 B1 | 11/2008 | Cohen |
| 7,630,774 B2 | 12/2009 | Karni et al. |
| 7,678,111 B2 | 3/2010 | Mulier et al. |
| 2004/0236203 A1 | 11/2004 | Salvo |
| 2005/0251032 A1 | 11/2005 | Smith |
| 2007/0208399 A1 | 9/2007 | Turner et al. |
| 2008/0262512 A1 | 10/2008 | Humayun et al. |
| 2010/0204560 A1 | 8/2010 | Salahieh et al. |
| 2011/0063189 A1 | 3/2011 | Cohen et al. |

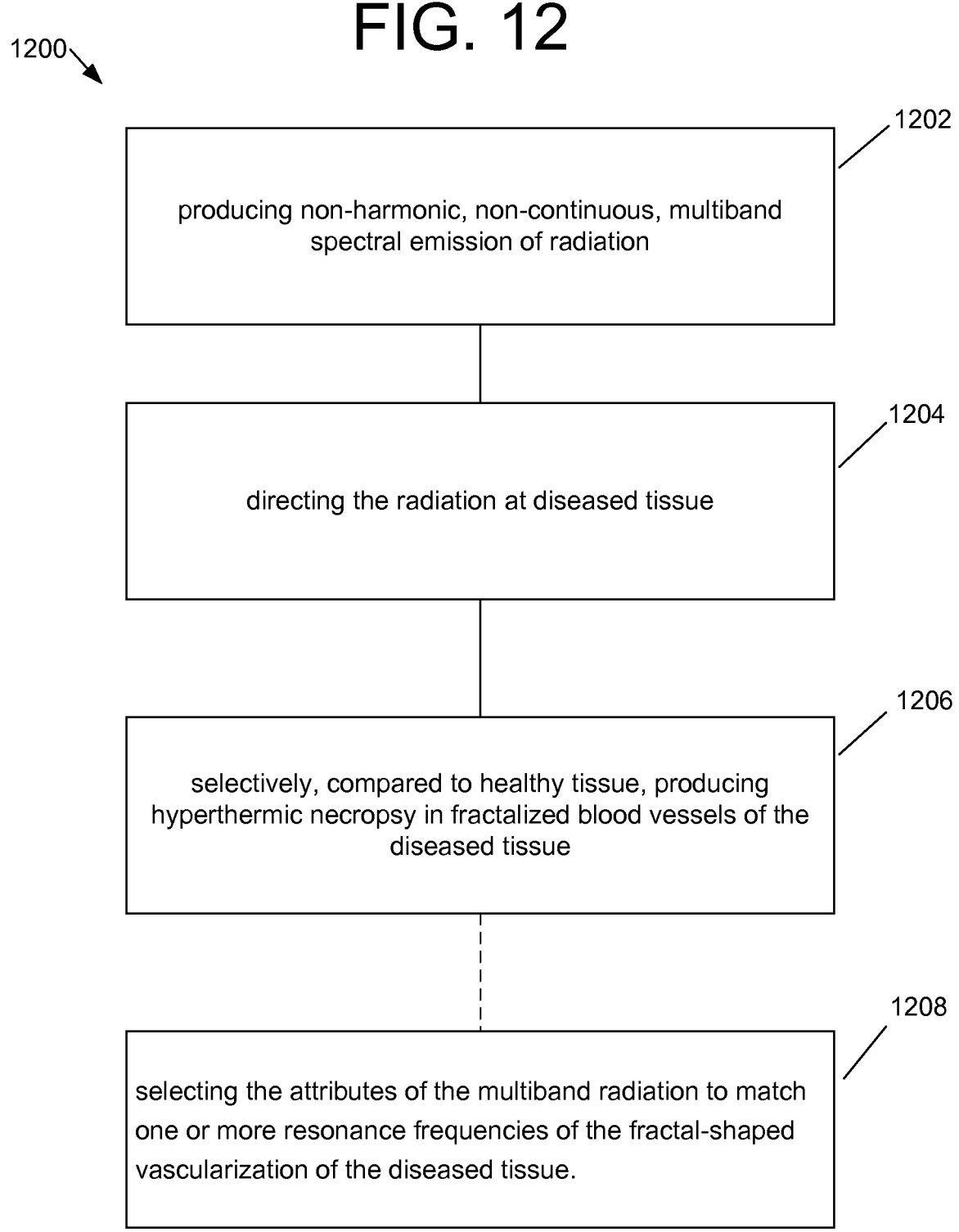

ONCOLOGICAL AMELIORATION BY IRRADIATION AND/OR ENSONIFICATION OF TUMOR VASCULARIZATION

RELATED APPLICATIONS

This application is a continuation of U.S. application Ser. No. 12/825,297, filed 28 Jun. 2010 and entitled "Oncological Amelioration by Irradiation and/or Ensonification of Tumor Vascularlization," which issued 5 May 2020 as U.S. Pat. No. 10,639,096, and which claims priority to U.S. Provisional Patent Application No. 61/269,622, filed 27 Jun. 2009 and entitled "Oncological Amelioration by Irradiation and/or Ensonification of Tumor Vascularization," the entire contents of which applications are incorporated herein by reference.

FIELD OF THE DISCLOSURE

This disclosure relates generally to the treatment of cancerous tissue or tumors, including using applied RF and/or ultrasonic energy to induce hyperthermia.

BACKGROUND OF THE DISCLOSURE

Surgical treatment of cellular tissues usually requires direct contact of target tissue with a medical instrument, usually exposing both the target and intervening tissue to substantial trauma. Often, precise placement of a treatment probe is difficult because of the location of a target tissue in the body or the proximity of the target tissue to obstructions or easily damaged, critical body organs, nerves, or other components.

High-frequency currents are used in electrocautery procedures for cutting human tissue, especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated. The frequency of the current for this use must be above about 300 kHz in order to avoid any adverse such as nerve and/or muscle responses.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a nondestructive level by conduction and convection forces of circulating fluids and other natural body processes.

Microwave, radiofrequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses and, more specifically, tissues in organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to kill the tissue constricting the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Chemotherapy generally involves systemic delivery of the therapeutic agents, the agents affecting both normal dividing and abnormal cells. Efforts to target neoplastic cells, such as with "bullets" comprising a neoplastic preferentially binding antibody coupled with a cytotoxic agent have had limited success; the agents are removed and concentrated by the liver in the removal process, exposing the liver to high levels of the toxin. Photodynamic therapy seeks to limit the cytotoxic activity to the areas exposed to light energy; however, since the photodynamic agents are administered systemically, epidermal areas exposed to light are also affected, requiring protection from the sun until the photodynamic agents are eliminated from the body.

Thus, while previous techniques have worked for the inducement of hyperthermia in cancerous tissue, other techniques are desirable.

SUMMARY

The present disclosure addresses limitations of previous cancer treatments techniques. Embodiments of the present disclosure are directed to techniques, including methods and systems/apparatus, that can be used to treat cancerous tissue by exploiting the fact that such tissue have vascular branching with fractal descriptions and fractal dimensions, which are different from those found in normal soft tissue vascular branching. Such fractal branching of diseased tissue can produce resonances, or preferential energy absorption, when irradiated by either ultrasound and/or radio frequencies of EM energy; these resonances are not shared by the vascularization in normal soft tissue. Accordingly, one or more specific arrangements of multiband radiation (e.g., RF and/or ultrasonic) used to irradiate such diseased tissue will cause heating and possibly localized necropsy of tumor blood vessels, with little or minimal damage to surrounding healthy tissue.

Embodiments can utilize ablation devices/techniques in conjunction with RF and/or ultrasonic sources. Embodiments can further utilize chemotherapy (before, during, or after hyperthermic treatment) for enhancing cancer treatment.

BRIEF DESCRIPTION OF THE DRAWINGS

Aspects of the present disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings:

FIG. 12 a block diagram of a method of treating diseased tissue, e.g., cancer tumors, in accordance with exemplary embodiments of the present disclosure.

Figure 1:
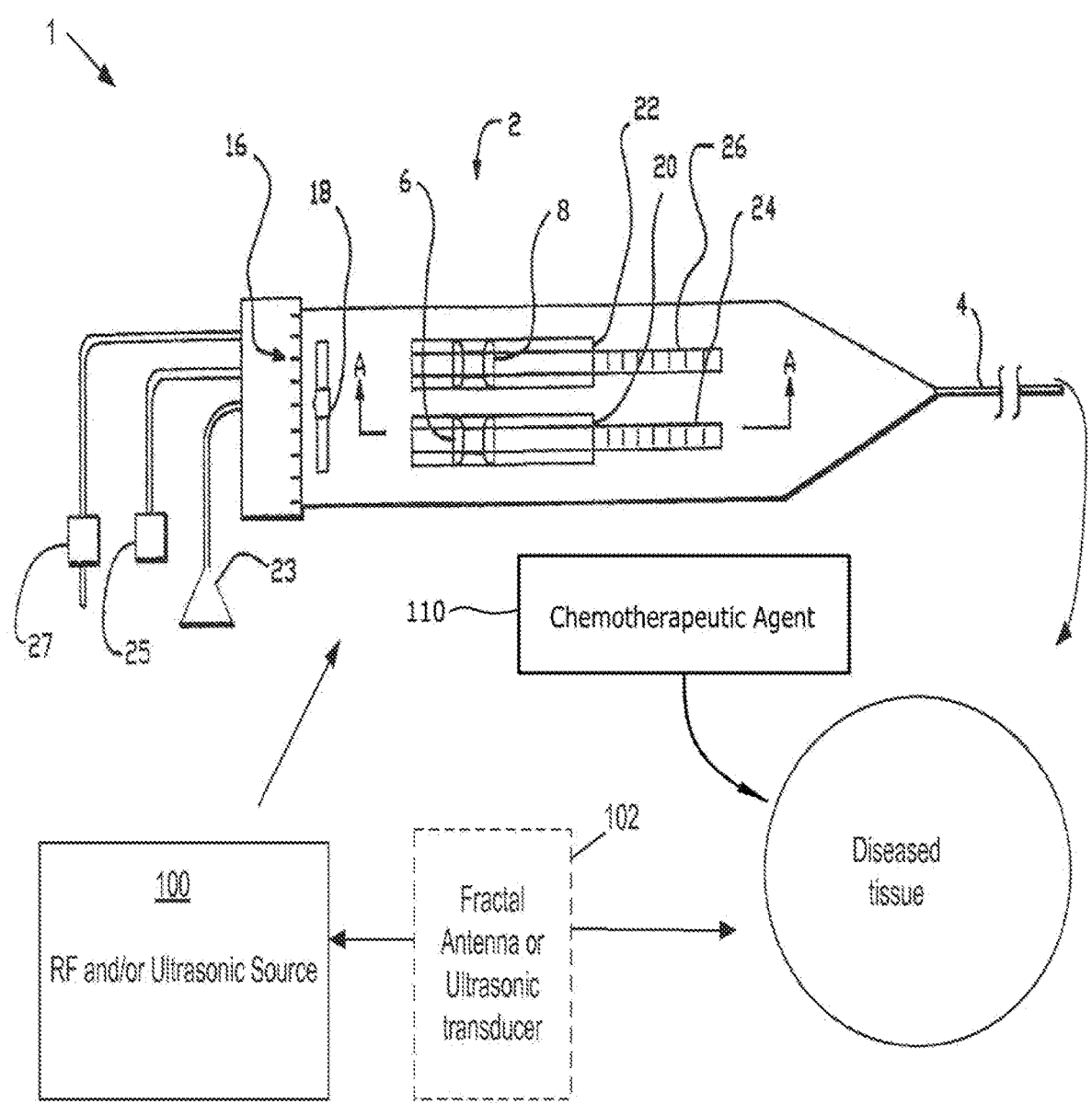
FIG. 1 is planar view of a stylet ablation device and energy source, in accordance with exemplary embodiments of the present disclosure.

While certain embodiments depicted in the drawings, one skilled in the art will appreciate that the embodiments depicted are illustrative and that variations of those shown, as well as other embodiments described herein, may be envisioned and practiced within the scope of the present disclosure.

DETAILED DESCRIPTION

While the present disclosure will be described more fully hereinafter with reference to the accompanying drawings, in which a particular embodiment is shown, it is to be understood at the outset that persons skilled in the art may modify the disclosure herein described while still achieving the favorable results of this disclosure. Accordingly, the description which follows is to be understood as a broad teaching disclosure directed to persons of skill in the appropriate arts and not as limiting upon the present disclosure.

Embodiments of the present disclosure are directed to techniques, including methods and systems/apparatus, that can be used to treat cancerous tissue by exploiting the fact that such tissue have vascular branching with fractal descriptions and fractal dimensions, which are different from those found in normal soft tissue vascular branching. Such fractal branching of diseased tissue can produce resonances, or preferential energy absorption, when irradiated by either ultrasound and/or radio frequencies of EM energy; these resonances are not shared by the vascularization in normal soft tissue. Accordingly, one or more specific arrangements of multiband radiation (e.g., RF and/or ultrasonic for "ensonification") used to irradiate such diseased tissue will cause heating and possibly localized necropsy of tumor blood vessels, with little or minimal damage to surrounding healthy tissue. Embodiments can utilize ablation devices in conjunction with RF and/or ultrasonic sources. Embodiments can further utilize chemotherapy (before, during, or after hyperthermic treatment) for enhancing cancer treatment.

Examples of suitable fractal shapes (for use for energy sources and/or electrodes) can include, but are not limited to, fractal shapes described in one or more of the following patents, owned by the assignee of the present disclosure, the entire contents of all of which are incorporated herein by reference: U.S. Pat. Nos. 6,452,553; 6,104,349; 6,140,975; 7,145,513; 7,256,751; 6,127,977; 6,476,766; 7,019,695; 7,215,290; 6,445,352; 7,126,537; 7,190,318; 6,985,122; 7,345,642; and, 7,456,799. Other suitable fractal shape for the resonant structures can include any of the following: a Koch fractal, a Minkowski fractal, a Cantor fractal, a torn square fractal, a Mandelbrot, a Caley tree fractal, a monkey's swing fractal, a Sierpinski gasket, and a Julia fractal, a contour set fractal, a Sierpinski triangle fractal, a Menger sponge fractal, a dragon curve fractal, a space-filling curve fractal, a Koch curve fractal, an lypanov fractal, and a Kleinian group fractal. Second-order deterministic fractals may be used in exemplary embodiments of electrodes.

Embodiments of the present disclosure can utilize a medical ablation device for localized therapeutic ablation to remove or reduce undesired tissue masses from remote locations in the body. With a suitably shaped rigid or flexible delivery tubes, the devices can be used with conventional delivery systems including scopes such laparoscopes, cystoscopes, and the like. With delivery tubes such a needles, the device with a memory shaped electrode can be used to ablated undesired tissue in orthopedic, neurological, gynecological and for less invasive surgical applications such as near zero surgical ablation of spinal discs to alleviate encroachment and pressure from herniated disks on adjacent nerves in the spinal column.

Figure 2:
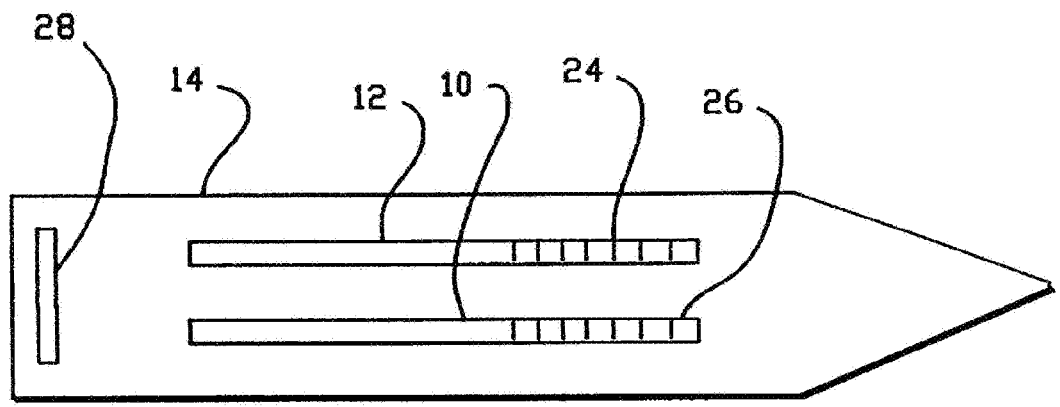
FIG. 2 is a top view of the handle top plate of the stylet ablation device shown in FIG. 1.

Referring to the drawings, FIG. 1 is a planar view of a stylet ablation device 1, according to exemplary embodiments of the present disclosure. The device 1 includes a handle portion 2 and a delivery tube portion 4 for application to diseased tissue, e.g., cancerous tumors. Stylet sleeve control manual tab 6 and stylet electrode control manual tab 8 are mounted for sliding engagement in slots 10 and 12 in the handle top plate 14 (FIG. 2). Index markings 16 indicate the relative angle of orientation of the stylet with respect to the stylet angle indicator 18. Angle indicator 18 can be a bubble in a curved transparent tube, a weighted pivot dial indicator or an electronic angle indicator. The position of the distal edges 20 and 22 of the tab slides 6 and 8 with their respective gauge reference strips 24 and 26 independently indicate the relative advancement and retraction of the stylet electrode and sleeve shown in FIGS. 2-4. A fiber optic connector 23, RF power connector 25, and ohmic resistance detector 27 are shown extending from the proximal end of the handle housing. While certain features are shown for the stylet 1, others may be used in addition or substitution.

With continued reference to FIG. 1, an energy source 100 is shown. The energy source 100 is functional to supply RF or ultrasonic energy for hyperthermic treatment of the diseased tissue. Of course when both RF and ultrasonic energy are provided, respective different sources may be used in combination. In preferred embodiments, the energy from the source(s) 100 is transmitted to the diseased tissue DT by way of a RF antenna or ultrasonic transducer 102 that has at least a portion with a fractal-shaped geometry to facilitate the production of multiband radiation for treatment of diseased tissue. In further exemplary embodiments, as described below, an RF electrode used within an ablation tip can have an electrode with at least a portion having a fractal-shaped geometry to facilitate the production of multiband radiation for treatment of diseased tissue. In other embodiments, the energy from the source(s) can be used, without use of an ablation device, for hyperthermic treatment of diseased tissue. A chemotherapeutic agent 110 may be used for treatment of diseased tissue DT, as described in further detail for FIG. 7.

FIG. 2 is a top view of the handle top plate of the stylet ablation device 1 shown in FIG. 1. Slots 10 and 12 receive the respective tabs 6 and 8 for sliding engagement therein. Slot 28 receives the stylet angle indicator.

Figure 3:
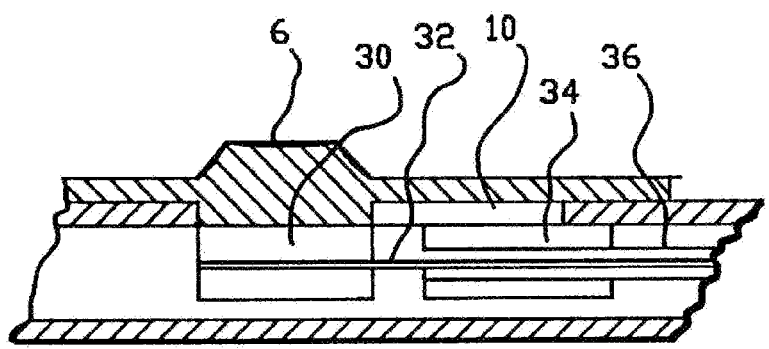
FIG. 3 is a fragmentary cross-sectional view of the manual control portion of the handle of the stylet ablation device shown in FIG. 1, taken along the line A-A in FIG. 1.

FIG. 3 is a fragmentary cross-sectional view of the manual control portion of the handle of the stylet ablation device shown in FIG. 1, taken along the line A-A. Manual electrode tab 6 is attached to an electrode connector 30 which is connected to the proximal end of the stylet electrode 32. Manual sleeve tab 8 (FIG. 1) is connected to a sleeve connector 34 which is connected to the proximal end of the sleeve 36.

The electrode 32 is preferably made of a flexible, shape memory metal such as nickel-titanium alloy or tempered steel. The sleeve is made of a highly conformable insulating plastic material such as polyimide. Other suitable materials may of course be used in addition or substitution. The electrode preferably includes one or more portions that have a fractal shape, to facilitate the production of multiband radiation for treatment of diseased tissue.

Simultaneous forward and rearward movement of the control tabs 6 and 8 effect simultaneous advancement and retraction of the treatment stylet. Individual movement of the control tabs 6 and 8 provide individual advancing and retracting movement of the respective sleeve and electrode. Indexing strips 24 and 26 provide reference points for controlled positioning of the sleeve control tabs 6 and 8, permitting precise, independent positioning of the stylet elements for controlled ablation of remote body portions as is explained in greater detail hereinafter.

Figure 4:
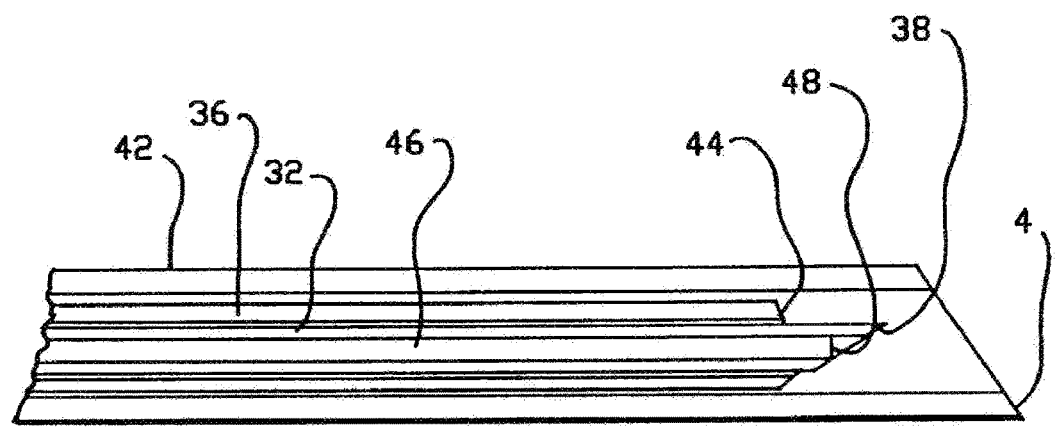
FIG. 4 is a fragmentary cross-sectional view of the tip of the stylet ablation device such as that shown in FIG. 1 with the stylet retracted into the tip.

FIG. 4 is a cross-sectional view of the tip of the stylet ablation device such as that shown in FIG. 1 with the stylet retracted into the tip for initial insertion to a position accessible with a straight needle. The electrode tip 38 is positioned behind the leading sharpened tip 40 of the needle or tube 42. The insulating sleeve tip 44 is positioned just behind the leading edge of the electrode tip 38.

When the electrode 32 is a hollow tube, it can be a conduit for aspiration during treatment, liquid deliver, or in the embodiment shown, a housing for a fiber optic 46. The polished fiber optic tip 48 is then positioned behind the electrode tip 38 to facilitate viewing of the tissue surrounding the electrode tip during insertion.

Figure 5:
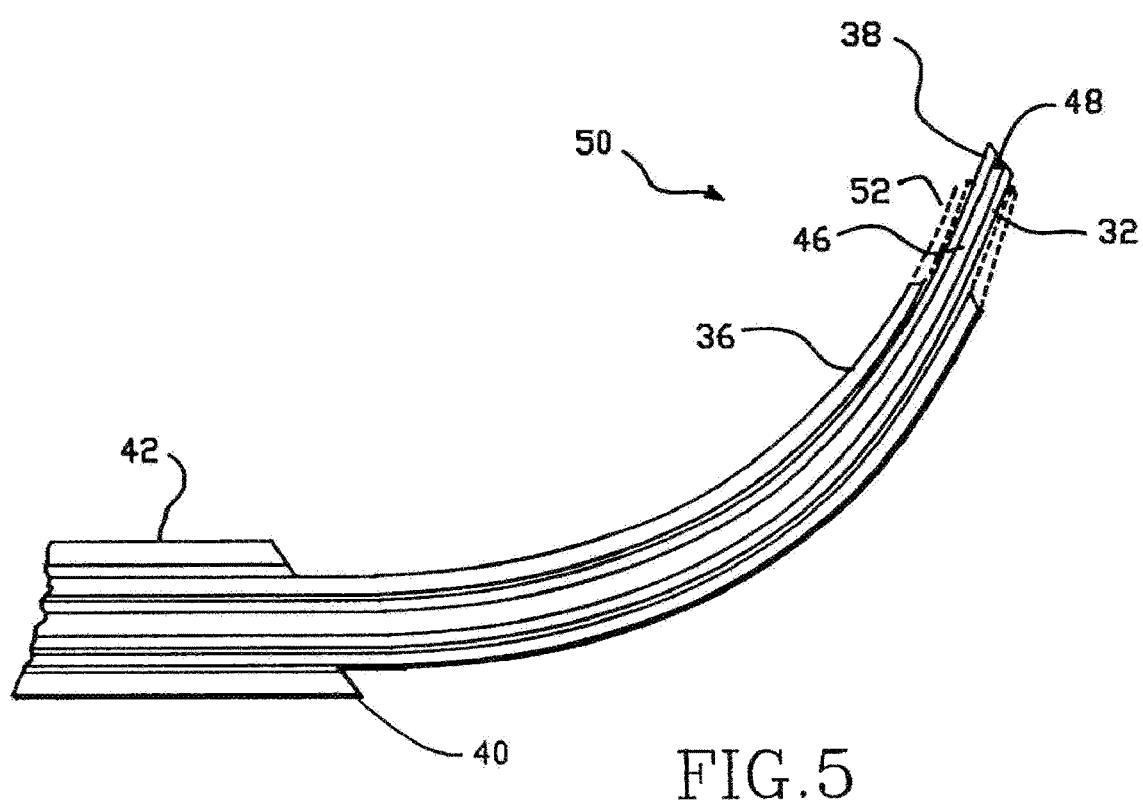
FIG. 5 is a fragmentary cross-sectional view of the tip of the stylet ablation device shown in FIG. 4 with the electrode and sleeve extended from the tip.

FIG. 5 is a cross-sectional view of the tip of the stylet ablation device shown in FIG. 4 with the electrode and sleeve extended. This embodiment shows a flexible stylet 50 having a predetermined curved configuration. The flexible stylet can also be straight, if the remote position can be reached by a straight path from the point of entry without damaging a vital body component. The electrode can be made of a shape memory alloy, shaped to the revert to a desired configuration when released from the tubing. The configuration can be simple curves, a combination of straight portions and curves, curves with differing radii, in two or three dimensions, selected to direct the electrode and its surrounding flexible, highly conformable sleeve in a preselected two or three dimensional path through tissue to a site to be ablated.

Methods for shaping shape memory alloys are well known in the art and are not a part of this disclosure. In general, the alloys are annealed with heat and then set in the desired memory shape by quick cooling the annealed electrode while maintaining it in the non-linear shape ultimately desired.

The sleeve 36 is initially in the dotted line position 52. Following insertion into the body to the specific site to be ablated, the sleeve 36 is withdrawn from a selected portion of the electrode 32 to the solid line position to expose the specific electrode area required to form a lesion of the desired size.

A method of this disclosure for medical ablation of difficult to access tissues comprising first inserting a hollow needle through a tissue layer, the needle enclosing a conductive electrode of highly flexible memory metal having a predetermined curved memory configuration and a sharpened distal terminus, the electrode tube being enclosed within an insulating sleeve axially moveable thereon and bendable therewith. Then the electrode and sleeve are advanced from the terminal end of the hollow needle, whereby the portion of the electrode and sleeve advanced beyond the end of the needle adopt the predetermined curved memory configuration and the electrode and sleeve follow a correspondingly predetermined curved path through tissue to the site to be ablated Then a portion of the sleeve is withdrawn from the terminus of the electrode to expose a predetermined electrode area for ablation. Finally, RF energy is applied to the tissue surrounding the exposed electrode area to effect ablation thereof.

Figure 6:
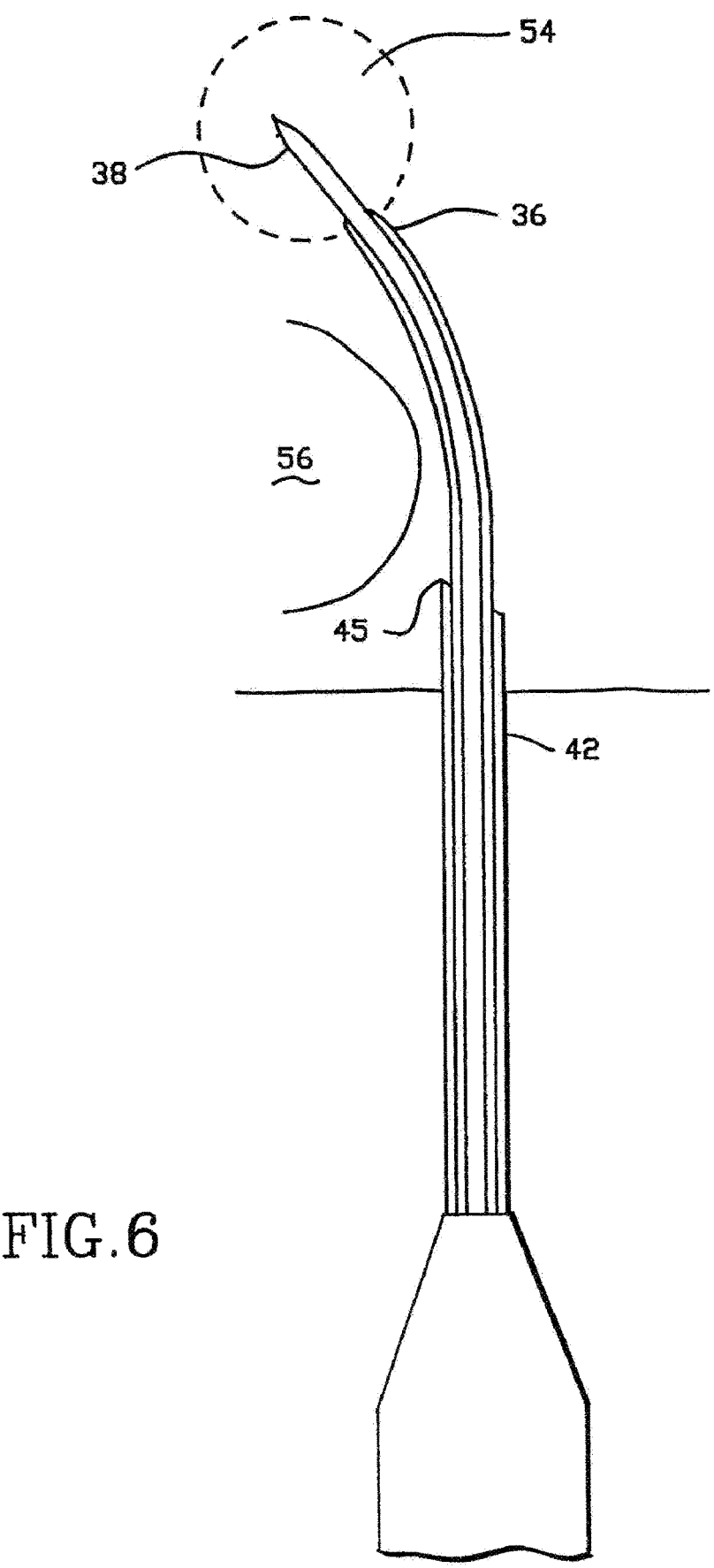
FIG. 6 is a schematic view showing use of an embodiment with a shape memory electrode preformed into a curved shape to ablate a tissue mass behind an obstacle such as a vertebra.

Referring to FIG. 6, use of an embodiment with a shape memory electrode preformed into a curved shape to ablate a near zero access area behind an obstruction in the body. The objective of the treatment is to reduce the size of the mass 54 behind a rigid obstacle such as bone 56 (or area to be protected from penetration). The electrical conductor and sleeve is extended from the needle 40 through surrounding tissue around the obstacle to its back surface, and the target tissue to be reduced. The sleeve 36 is then withdrawn to a position exposing the electrode area required to ablate the tissue mass. Heat is generated in the target tissue from an electric current or electromagnetic field produced by the electrical conductor. Preferably, the volume of tissue being treated is controlled by moving the non-conductive sleeve to expose a selected length of electrode in the body tissue to be treated, the remaining area of the electrode remaining shielded by the sleeve to protect the intervening tissues. The amount and duration of the energy delivery is also varied to control the volume of tissue being treated. The current passes to a large surface area grounding plate contacting the outer skin surface.

Figure 7:
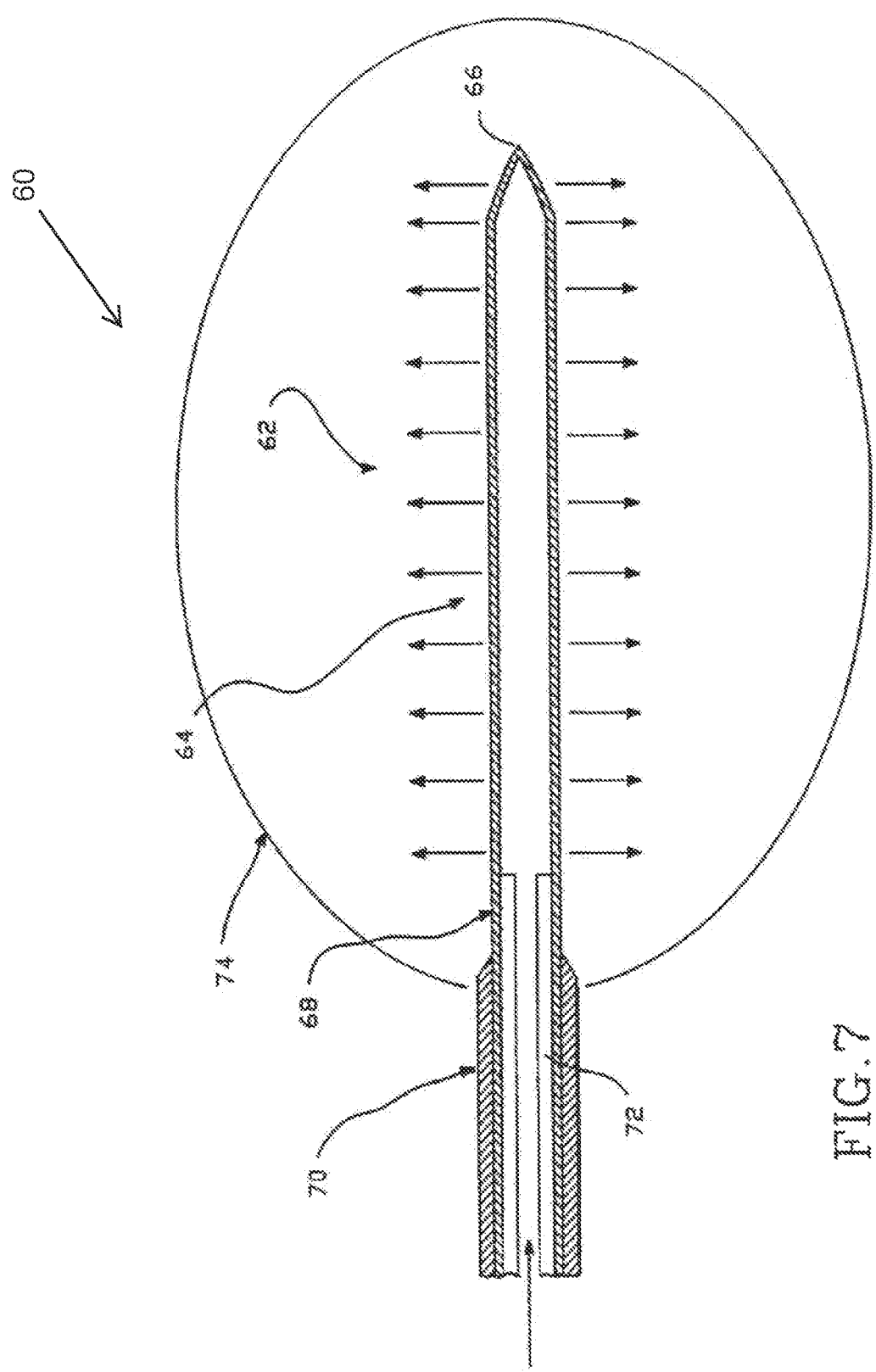
FIG. 7 is a cross-sectional view of a RF stylet including chemotherapy agent distributors.

FIG. 7 is a cross-sectional view of a RF stylet including chemotherapy agent distributors of this disclosure. In this embodiment, the stylet 60 includes an electrode 62 having the configuration of a tube 64 with a sharp-tipped, closed distal end 66 and a plurality of fluid outlet openings 68, distributed along the length of the exposed electrode portion. The electrode 62 is enclosed within an insulating sleeve 70 which is longitudinally slidable on the electrode, as described above, to control the length and surface of electrode exposed to the surrounding tissue. The tube can optionally contain an inner un-perforated tube 72, the position of which can be adjusted to expose a selected number of fluid distribution ports. The treatment fluid flows outwardly through the distribution ports as shown by the arrows extending outwardly there from.

The stylet 60 is advanced to the tissue to be ablated, and the sleeve 70 is withdrawn, exposing a controlled length of electrode and selected number of fluid distribution ports. RF energy is applied, raising the temperature in the lesion site to a temperature of above 45 degree for creating an infusion barrier capsule 74, the temperature can be from about 45 degree C. to 170 degree C. and is preferably from about 80 degree C. to 120 degree C. The desiccation boundary 74 acts as a barrier to fluid flow, forming a capsule and restraining escape of fluid introduced through the ports.

In one embodiment of the method of this disclosure, the infusion boundary is created before fluid is introduced, to restrain its escape from beyond the ablation zone. In another embodiment, the fluid introduction precedes or is concurrent with the application of RF energy, whereby the heating facilitates and increases the penetration of the tissue by the chemotherapeutic fluid. It will be readily apparent to a person skilled in the art that other variations and sequences, and repetitions thereof, can be applied within the scope of this disclosure to control the zone of treatment and fluid delivery according to the physician's desired objective.

Figure 8A:
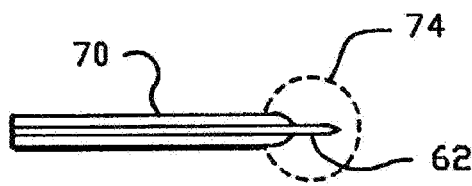
FIGS. 8a, 8b and 8c are schematic views of tissue undergoing capsular ablation according to this disclosure, demonstrating sleeve adjustments of the device of FIG. 7 to effect a desired ablation lesion geometry.
Figure 8B:
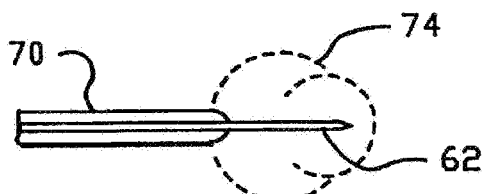
Figure 8C:
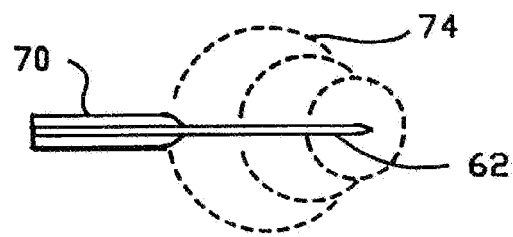

FIGS. 8a, 8b and 8c are schematic views of tissue undergoing capsular ablation according to this disclosure, demonstrating sleeve adjustments of the device of FIG. 7 to effect a desired ablation lesion geometry. FIG. 8a shows an initial lesion formed with a short portion of electrode 62 extending beyond the insulating sleeve 70. In FIG. 8b, the sleeve 70 has been retracted to expose a longer portion of electrode 62, producing a lesion with a larger radius, pronounced in the portion which beyond the infusion barrier formed in the ablation of FIG. 8a. In FIG. 8c, the sleeve 70 has been retracted to expose a still longer portion of electrode 62, producing a lesion with a still larger radius, pronounced in the portion which beyond the infusion barriers formed in the ablations of FIGS. 8a and 8b. The ultimate lesion barrier has an approximately, overall conical configuration.

Figure 9A:
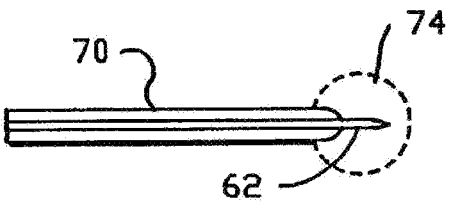
FIGS. 9a, 9b, 9c and 9d are schematic views of tissue undergoing capsular ablation according to this disclosure, demonstrating stylet position adjustment of the device of FIG. 7 to effect a desired ablation lesion geometry.
Figure 9B:
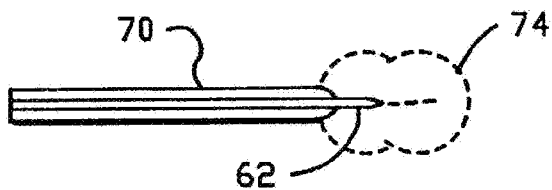
Figure 9C:
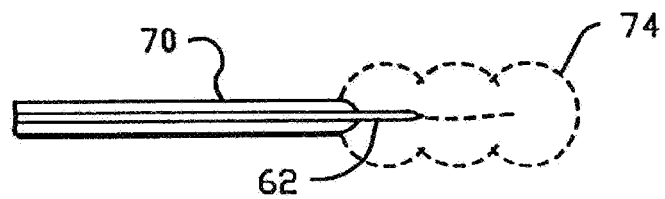
Figure 9D:
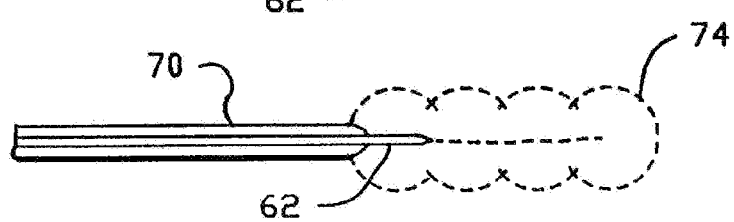

FIGS. 9a, 9b, 9c and 9d are schematic views of tissue undergoing capsular ablation according to this disclosure, demonstrating stylet position adjustment of the device of FIG. 7 to effect a desired ablation lesion geometry. FIG. 9a shows an initial ablation lesion formed with the stylet extending to a maximally distal position and with a small portion of the electrode 62 extended beyond the insulating sleeve 70. FIGS. 9b, 9c and 9c show successive positions and overlapping lesions formed by incrementally retracting the stylet in the proximal position, performing an ablation at each incremental position to provide an ultimate lesion barrier having an approximately, overall cylindrical configuration.

It will be readily apparent to a person skilled in the art that other sequences, including combinations of sequences illustrated in FIGS. 8a, 8b and 8c, and in FIGS. 9a, 9b and 9c can be devices without departing from the spirit and scope of this disclosure, and all of these combinations and variations are considered to be within the scope of this disclosure.

Figure 10:
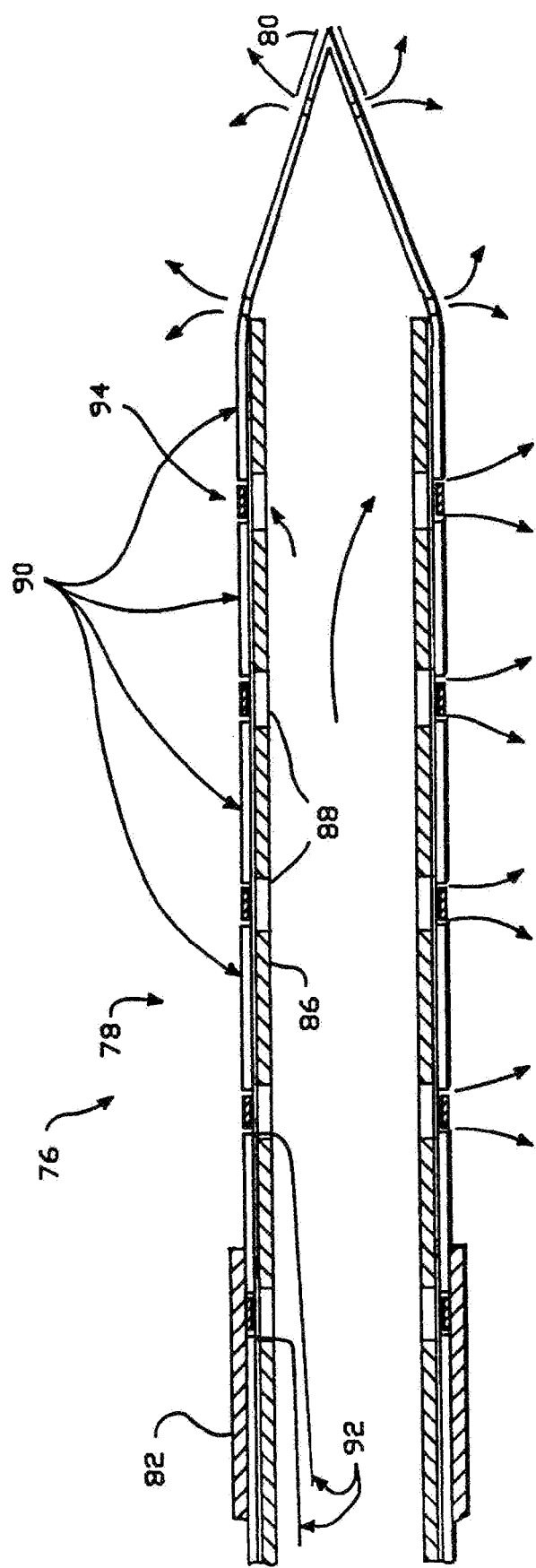
FIG. 10 is a cross-sectional view of an alternate embodiment of a RF stylet including chemotherapy agent distributors and a plurality of annular electrode conductors.

FIG. 10 is a cross-sectional view of an alternate embodiment of a RF stylet including chemotherapy agent distributors and a plurality of annular electrode conductors. In this embodiment, the stylet 76 comprises an electrode and distribution outlet bearing section 78 with a closed sharpened tip 80 and an insulating sleeve 82 longitudinally moveable thereon. The electrode section comprises an inner support tube 86 with fluid distribution ports 88 spaced along its length. Between each pair of ports 88 are positioned conductive sleeve segments or annular coatings 90. Each conductive sleeve segment 90 is connected to an individual insulated electrical RF power lead 92 connected to a switching and power delivery console (not shown). Suitable power supplies are described in U.S. Pat. No. 5,385,544 issued Jan. 31, 1995, the entire contents of which are hereby incorporated by reference. Between each conductive sleeve segment 90 is positioned an annular insulating sleeve or ring 94. Fluid passing outwardly through the ports 88 pass between the conductive sleeves segments 90 and the insulating rings 94 to pass outward into the surrounding tissue as shown by the arrows extending outwardly from the spaces between the sleeve segments 90 and rings 94.

A further aspect of the present disclosure is directed to surfaces that include dual-use or multiple-use apertures for application of multi-band energy to diseased tissue.

Figure 11:
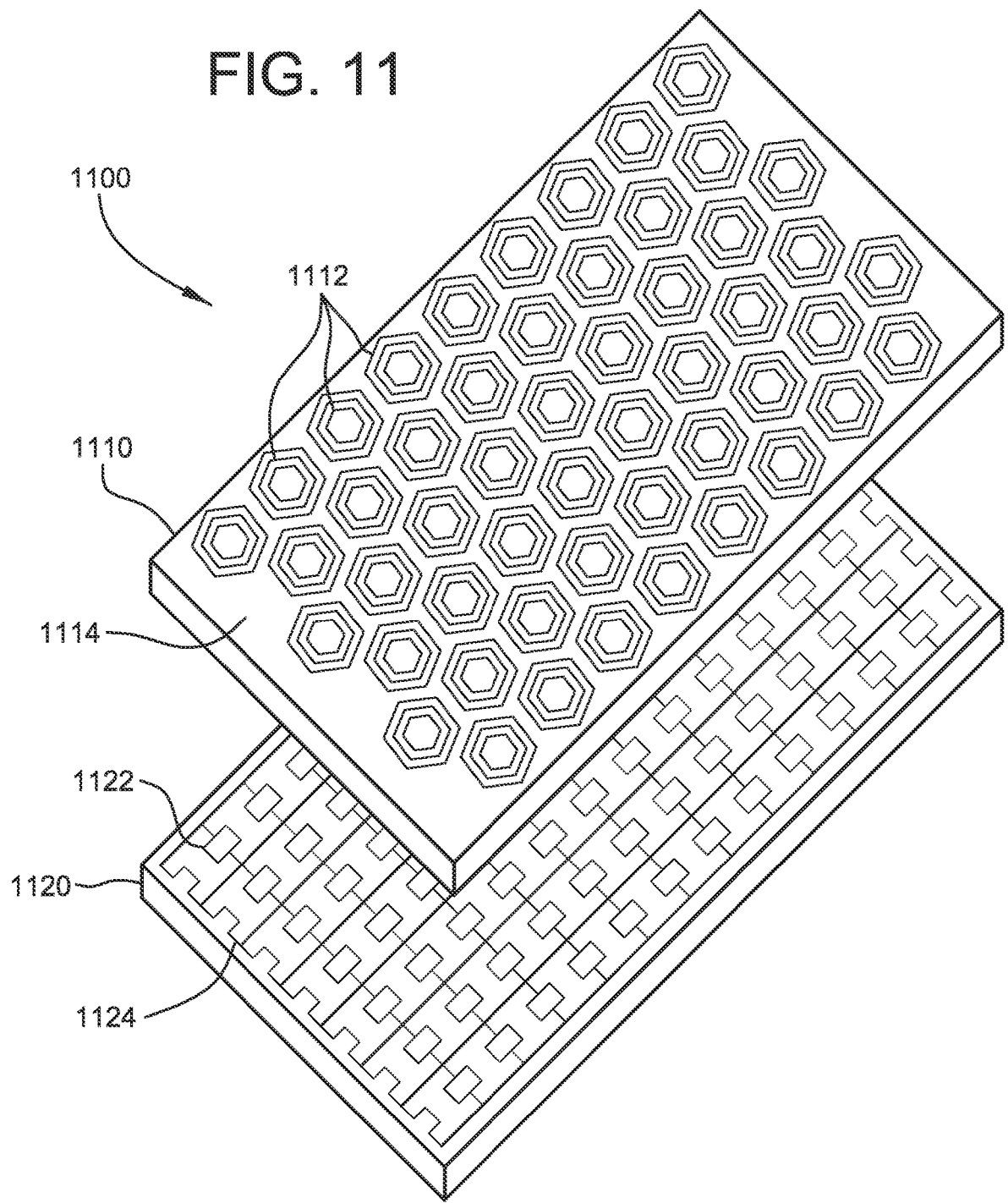
FIG. 11 depicts an exploded view of an aperture engine surface, in accordance with alternate embodiments of the present disclosure.

FIG. 11 depicts an exploded view of a so-called aperture engine surface 1100, in accordance with alternate embodiments of the present disclosure. Such a surface, e.g., as used for an RF or ultrasonic transmitter or in an ablation electrode, can be used to transmit multi-band energy to diseased tissue for hypothermic treatment.

FIG. 11 depicts an embodiment of such a surface 1100, which can include multiple layers, e.g., a first layer of antenna arrays 1110, and a second layer of a metal-fractal backplane player 1120. Since the apertures for such embodiments can provide multiple functions such as collecting power (e.g., from nearby or connected antennas) and then transmit the energy as RF radiation, they can be referred to as "engines" that depend on an "aperture," hence the term "aperture engine."

With continued reference to FIG. 11, the antenna array layer 1110 may be composed of or include an array of antennas 1112 on a dielectric substrate 1114. The antennas 1112 can include fractal antennas/resonators, which can afford higher gain for the given aperture. The fractal antennas 1112 can be of a desired shape or include a desired fractal generator (e.g., a Sierpinski triangle or square, Koch, Hilbert, torn-square, Mandelbrot, Minkowski, which can be open or island forms). It should be noted that the elements depicted for the antenna layer in FIG. 11 are representative of individual fractals of desired shape (such as those just listed). The metal-fractal (Met-fractal) backplane layer 1120 can be treated or considered the same way. In other words, fractal antennas 1122 of desired shape (e.g., fractal generator and dimensions) on a dielectric substrate 1124 can be used. Other embodiments can of course be included within the scope of the present disclosure. Moreover, other shapes of panels and/or antennas of the antenna array layer and/or fractal elements of the Metfractal Backplane Layer and/or solar cell layer may be used.

Power ranges, fluence values, application times, and radiation frequencies (RF and/or ultrasonic) can be selected as desired based on desired treatment and safety parameters, and the like. For example, suitable RF frequencies can include, but are not limited to, 1-100 MHz, inclusive of any sub-range within such range. Examples of various RF power levels are described in U.S. Pat. Nos. 5,599,345; 7,678,111; and, in U.S. Pat. No. 7,630,774; the entire contents of all of which are incorporated herein by reference. For further example, suitable ultrasonic frequencies can include, but are not limited to, 1-50 MHz, inclusive of any sub-range within such range. Suitable ultrasonic materials (e.g., transducers) and operational parameters are described in U.S. Pat. Nos.

7,326,201; 7,179,254; and, U.S. Patent Publication No. 2008/0262512; the entire contents of all of which are incorporated herein by reference.

FIG. 12 depicts a block diagram of a method 1200 of treating diseased tissue, e.g., cancer tumors, in accordance with exemplary embodiments of the present disclosure. For the method of treatment, non-harmonic, non-continuous, multiband spectral emission of radiation can be produced, as described at 1202. The radiation can be directed at diseased tissue, as described at 1204. Then, selectively, compared to healthy tissue, hyperthermic necropsy can be produced or effected in fractalized blood vessels of the diseased tissue, as described at 1206. Accordingly, such multi-band transmissions, by being selected and matched to resonances of the fractalized blood vessel structures in the diseased tissue, cause those fractalized blood vessel structures to overheat/overvibrate and undergo destruction/necropsy.

In exemplary embodiments, the radiation produced for method 1200 is RF radiation. The radiation produced can be ultrasonic radiation as well. As described at 1208, the attributes of the multiband radiation (frequency ranges) can be selected to match one or more resonance frequencies of the fractal-shaped vascularization of the diseased tissue so that heating of the tissue is effected. For method 1200 and like embodiments, systems/apparatus described herein can be utilized.

The devices, systems, and methods of this disclosure can provide the physician with a flexible variety of ablation procedures, optionally combining application of ablation energy to elevate tissue temperature with the treatment zone to above 45 degree C. to cause death of cells therein, and possibly in combined therapy with fluid applications. For example, application of saline fluid can reduce desiccation of tissue adjacent the electrode surfaces.

Application of chemotherapeutic substances before application of the ablation energy can exploit the effects of the heating the tissue and the fluid to increase distribution of the fluid in the adjacent tissues. Application of chemotherapeutic substances after ablation forming an encapsulated lesion can reduce distribution of the chemotherapeutic agent to tissue beyond the ablation capsule, concentrating its activity to the tissues within the capsule and reducing and almost eliminating the systemic effects of the treatment. These alternatives and combinations thereof provide to a physician treating tissue containing neoplastic cells a wide range of alternatives. A treatment regimen can include use of devices combining any of these alternatives or all of them to increase the effectiveness of the treatment.

Embodiments of the present disclosure can be used in combination with systemic or localized chemotherapy.

Examples of chemotherapeutic agents suitable for use in the method of this disclosure include, but are not limited to anti-neoplastic agents. Suitable anti-neoplastic agents include, but are not limited to alkylating agents including alkyl sulfonates such as Busulfan, Improsulfan and Piposulfan; aziridines such as Benzodepa, Carboquone, Meturedepa and Uredepa; ethylenimines and Methylmelamines such as Altretamine, Triethylenemelamine, Triethylenephosphoramide, Triethylenethiophosphoramide and Trimethylolmelamine; nitrogen mustards such as Chlorambucil, Chlornaphazine, Cyclophosphamide, Estramustine, Ifosfamide, Mechlorethamine, Mechlorethamine Oxide Hydrochloride, Melphalan, Novembichin, Phenesterine, Prednimustine, Trofosfamide and Uracil Mustard; nitrosoureas such as Carmustine, Chlorozotocin, Fotemustine, Lomustine, Nimustine, Ranimustine; and others such as Dacarbazine, Mannomustine, Mitobronitol, Mitolactol and Pipobroman. Also included are antineoplastic antibiotics such as Aclacinomycines, Actinomycin, Anthramycin, Azaserine, Bleomycins, Cactinomycin, Carubicin, Carzinophilin, Chromomycins, Dactinomycin, Daunorubicin, 6-Diazo-5oxo-L-norleucine, Doxorubicin, Epirubicin, Mitomycins, Mycophenolic Acid, Nogalamycin, Olivomycins, Peplomycin, Plicamycin, Porfiromycin, Puromycin, Streptonigrin, Streptozocin, Tubercidin, Ubenimex, Zinostatin and Zorubicin. Also included are antineoplastic antimetabolites such as folic acid analogs such as Denop-terin, Methotrexate, Pteropterin and Trimetrexate; purine analogs such as Fludarabine, 6-Mercaptopurine, Thiamiprine and Thioguanine; pyrimidine analogs such as Ancitabine, Azacitidine, 6-Azauridine, Carmofur, Cytarabine, Doxifluridine, Enocitabine, Floxuridine, Fluorouracil and Tegafur; enzymes such as L-Asparaginase; and others such as Aceglatone, Amsacrine, Bestrabucil, Bisantrene, Carboplatin, Cisplatin, Defosfamide, Demecolcine, Diaziquone, Eflornithine, Elliptinium Acetate, Etoglucid, Eto-poside, Gallium Nitrate, Hydroxyurea, Interferon-.alpha., Interferon.beta., Interferon.gamma., Interleukin-2, Lentinan, Lonidamine, Mitoguazone, Mitoxantrone, Mopidamol, Nitracrine, Pentostatin, Phenamet, Pirarubicin, Podophyllinic Acid; 2-Ethylhydrazide, Procarbazine, PSK, Razoxane, Sizofiran, Spirogermanium, Taxol, Teniposide, Tenuazonic Acid, Triaziquone, 2,2',2"-Trichlorotriethylamine, Urethan, Vinblasine, Vincristine and Vindesine.

One skilled in the art will appreciate that embodiments and/or portions of embodiments of the present disclosure can be implemented in/with computer-readable storage media (e.g., hardware, software, firmware, or any combinations of such), and can be distributed and/or practiced over one or more networks. Steps or operations (or portions of such) as described herein, including processing functions to derive, learn, or calculate formula and/or mathematical models utilized and/or produced by the embodiments of the present disclosure, can be processed by one or more suitable processors, e.g., central processing units ("CPUs") implementing suitable code/instructions in any suitable language (machine dependent on machine independent).

While certain embodiments and/or aspects have been described herein, it will be understood by one skilled in the art that the methods, systems, and apparatus of the present disclosure may be embodied in other specific forms without departing from the spirit thereof. For example, known imaging techniques can be used with embodiments of the present disclosure for precise application of energy to diseased tissue.

For example, while certain wavelengths/frequencies of operation have been described, these are merely representative and other wavelength/frequencies may be utilized or achieved within the scope of the present disclosure.

Furthermore, while certain preferred fractal shapes have been described others may be used within the scope of the present disclosure. Moreover, while fractal shapes have been described for use in radiation transmission herein, other embodiments of the present disclosure can rely on non-fractal shapes for radiation transmission for hyperthermic treatment of diseased tissue. Accordingly, the embodiments described herein are to be considered in all respects as illustrative of the present disclosure and not restrictive.

What is claimed is:

1. A multiband RF transmitter system for amelioration and reduction of diseased tissue, the multiband RF transmitter system comprising:

an energy source configured and arranged to produce radiofrequency (RF) energy wherein the RF energy includes non-harmonic noncontinuous multiband spectral radiation adapted to a fractal shaped vascularization of the diseased tissue; and a transmitter configured to deliver the RF energy produced by the energy source and to direct the RF energy to a location including the diseased tissue for heating of the diseased tissue;

wherein the transmitter includes an RF antenna;

wherein at least a portion of the RF antenna has a fractal shape, wherein the fractal shape is a second order or greater deterministic fractal, so as to produce an arrangement of frequency bands adapted to resonances of the fractal shaped vascularization of the diseased tissue; and wherein the noncontinuous multiband spectral radiation is adapted to match one or more of the resonances of the fractal shaped vascularization of the diseased tissue for producing heating when the fractal shaped vascularization of the diseased tissue is irradiated by the noncontinuous multiband spectral radiation.

2. The system of claim 1, wherein the energy source is configured to produce the noncontinuous multiband spectral radiation within a range of 2-2000 MHz.

\* \* \* \* \*